(12) United States Patent
Barstow

(10) Patent No.: US 7,455,519 B1
(45) Date of Patent: Nov. 25, 2008

(54) ANTI-FOG DENTAL MIRROR

(76) Inventor: Ricky A. Barstow, 2181 Bloomfield Rd., Cambridge, OH (US) 43725

( * ) Notice: Subject to any disclaimer, the term of this patent is extended or adjusted under 35 U.S.C. 154(b) by 122 days.

(21) Appl. No.: 11/448,934

(22) Filed: Jun. 8, 2006

(51) Int. Cl.
- *A61B 1/24* (2006.01)
- *A61B 1/267* (2006.01)
- *A61B 1/00* (2006.01)
- *A61C 1/00* (2006.01)
- *A61C 9/00* (2006.01)

(52) U.S. Cl. .............................. 433/31; 433/30; 433/31; 433/37; 600/189; 600/247; 600/248

(58) Field of Classification Search ............. 433/29–31, 433/80, 82, 141, 216; 359/871, 881, 882, 359/883; 600/189, 247–248
See application file for complete search history.

(56) References Cited

U.S. PATENT DOCUMENTS

| | | | | |
|---|---|---|---|---|
| 3,158,935 A | * | 12/1964 | Rosenthal | 433/30 |
| 3,692,387 A | * | 9/1972 | Bowman et al. | 359/606 |
| 5,827,059 A | * | 10/1998 | Nykaza | 433/30 |
| 2005/0180807 A1 | * | 8/2005 | Walsh, III | 401/131 |

* cited by examiner

*Primary Examiner*—Cris L Rodriguez
*Assistant Examiner*—Yogesh Patel
(74) *Attorney, Agent, or Firm*—Renner, Kenner, Greive, Bobak, Taylor & Weber

(57) ABSTRACT

A dental mirror includes a mirror assembly and a handle having an interior cavity. The handle further includes a non-circular aperture proximate one end, which communicates with the interior cavity. A push-arm extends through the aperture toward the mirror assembly and has a non-circular shape. The push-arm also has a wiper support, and a sponge is secured within the wiper support. The push-arm is selectively movable to carry the sponge over the mirror assembly, and the aperture prevents relative rotation of the push-arm.

11 Claims, 6 Drawing Sheets

ANTI-FOG DENTAL MIRROR

TECHNICAL FIELD

The present invention relates generally to a dental mirror, and more particularly to a dental mirror including a retractable wiper sponge which deposits anti-fog solutions on the mirror.

BACKGROUND ART

At room temperature dental mirrors tend to "fog up" when placed inside a patient's warm, humid mouth. Prior methods of preventing mirror fog up included dipping the mirror into a mirror de-fogging solution before insertion into the mouth. The thin film of solution left on the mirror's glass surface thereafter improved visibility for the operator. This event, however, is sometimes short lived because the moment the dentist, hygienist, or dental assistant uses a hand-piece drill, or air and water syringe, the thin film of solution left on the mirror surface is disrupted. The aforementioned high speed dental hand-pieces spray water to cool and flush tooth debris from the operative site. Also, air and water syringes are used to flush and aid in clearing the debris at the operative site. Consequently, during most routine dental procedures, the thin clear film of anti-fog solution on the dental mirror surface is disrupted and splattered with debris. Once the mirror surface is disrupted, it is useless to visualize the operative site.

A typical dental procedure involves using a dental hand-piece drill and a dental mirror. The procedure to clean and prepare a conventional dental mirror during a normal dental procedure generally takes seven to ten seconds. To clear and prepare a conventional dental mirror once it is splattered with debris, the operator must remove the mirror with one hand, put the hand-piece down in the other hand, pick up a wet gauze saturated with mirror defogger, wipe the mirror surface with the wet gauze, dip the mirror into the mirror defogger seated on a dental tray, wick the excess drops from the mirror, return the mirror to the mouth, pick up the hand piece, return it to the patient's mouth and continue the tooth preparation or other operative procedure. Such a procedure is time consuming and inefficient and often times the mirror is splattered again within seconds.

Another option some dentists use to improve visibility through the mirror is to have a dental assistant constantly spray water onto the mirror surface and suction the water simultaneously from the mouth. The success of this procedure to improve visibility is directly related to the assistant's ability and to the sensitivity of the patient's gag reflex. Some patients can not tolerate oral fluids accumulating within their oral cavity because their soft palate does not seal well against their tongue to prevent fluids from making their way into the throat. This naturally causes coughing and/or a gag reflex that interferes with the patient's comfort. Further, the coughing and gag movement make procedures more difficult for the dentist. In addition, many dental procedures require a dry field since they involve adhesive bonding. In those cases, the water spraying procedure to clear the dental mirror is not an option.

Thus, it is evident that a need exists in the art for a dental mirror which simplifies and expedites the cleaning process.

DISCLOSURE OF THE INVENTION

It is an object of the present invention to provide a dental mirror which may be quickly and easily cleaned.

It is another object of the present invention to provide a dental mirror which easily applies a coating of anti-fog solution on the mirror surface.

These and other objects of the present invention, as well as the advantages thereof over existing prior art forms, which will become apparent from the description to follow, are accomplished by the improvements hereinafter described and claimed.

In general, a dental mirror includes a mirror assembly, a handle having an interior cavity and a non-circular aperture proximate one end, the aperture communicating with the interior cavity, a push-arm extending through the aperture toward the mirror assembly, the push-arm having a non-circular shape, the push-arm also having a wiper support, and a wiper secured within the wiper support, wherein the push-arm is selectively movable to move the wiper over the mirror assembly, the aperture preventing relative rotation of the push-arm.

In another embodiment, a hand held dental mirror includes a handle adapted to be gripped by the hand, a mirror assembly disposed proximate to one end of the handle, a push-arm carrying a wiper, the push-arm movable to carry the wiper across the mirror assembly, wherein the push-arm is composed of a resilient material which deflects as the wiper is carried over the mirror assembly.

In yet another embodiment, a dental mirror comprising a handle having an elongate body portion defining an interior cavity, the elongate body portion having first and second openings at the opposed ends of the elongate body portion, the handle further including an elongate slot which communicates with the interior cavity, an insert received in the first opening and including at least one lug, a slider slidably received in the interior cavity and including a hook, a thumb tab slidably coupled to the elongate body portion and including a post which extends through the elongate slot, a push-arm extending through the second opening and carrying a wiper thereon, and a mirror assembly positioned proximate the second opening and adapted to reflect light, wherein forward movement of the thumb tab correspondingly causes forward movement of the push-arm and the slider.

A preferred exemplary dental mirror according to the concepts of the present invention is shown by way of example in the accompanying drawings without attempting to show all the various forms and modifications in which the invention might be embodied, the invention being measured by the appended claims and not by the details of the specification.

PREFERRED EMBODIMENT FOR CARRYING OUT THE INVENTION

Figure 1:
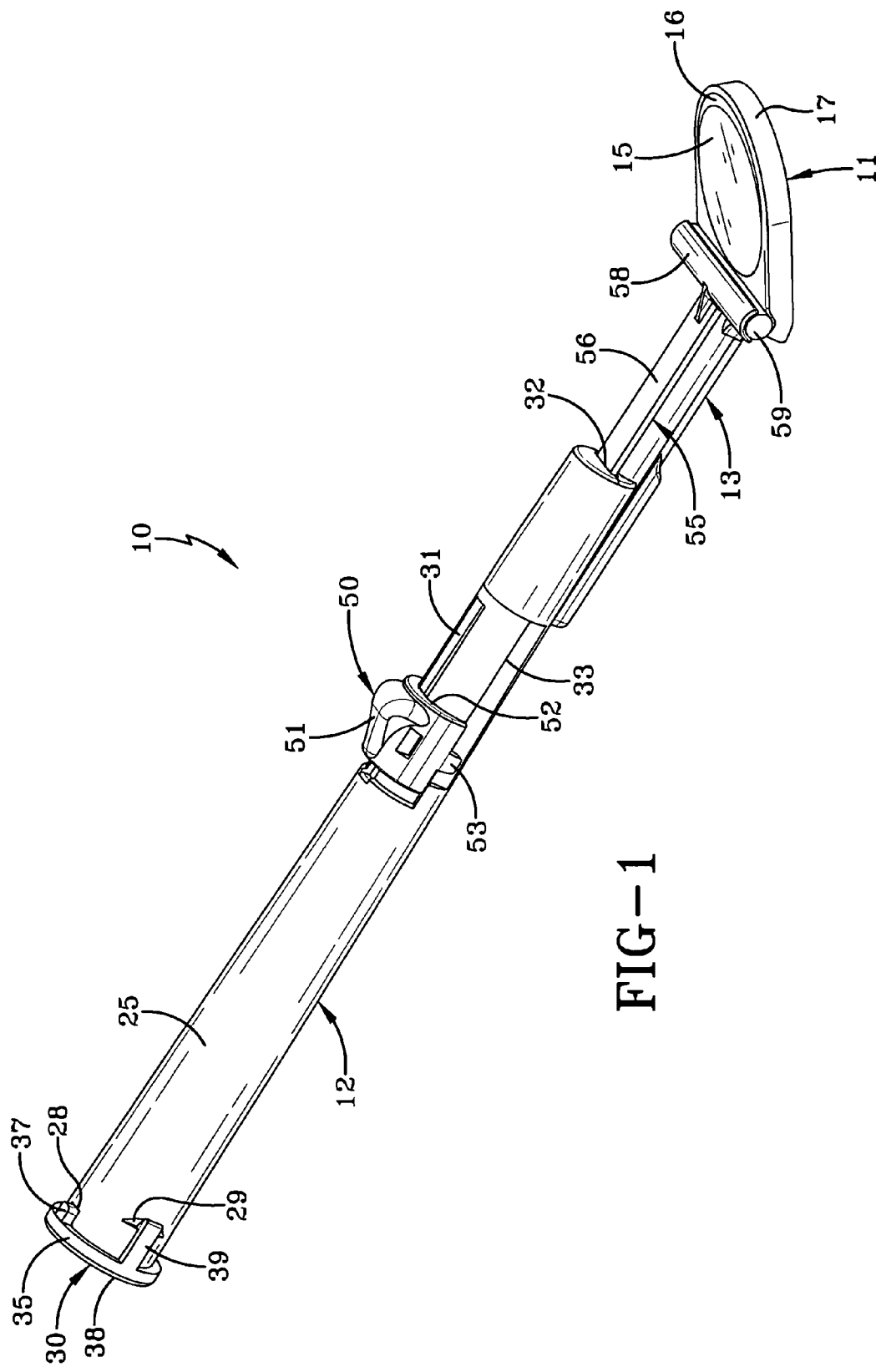
FIG. 1 is a perspective view of the dental mirror of the present invention.

Referring now to FIG. 1, a dental mirror, generally indicated by the numeral 10, includes a mirror assembly generally indicated by the numeral 11. Mirror assembly 11 is attached to a handle 12 via a stem 13 and is disposed at an angle α relative to stem 13 to provide promote visibility within an oral cavity. In a particularly preferred embodiment, angle α may be from about 15 to 20 degrees. However, it should be appreciated that mirror assembly 11 may be disposed at any angle α, depending upon the application or procedure.

Referring to FIGS. 1-4, mirror assembly 11 includes a mirror 14 which has a reflective surface 15 adapted to reflect light and provide visibility within the oral cavity. The mirror 14 is secured to a housing 16 via any means known in the art. For example, mirror 14 may be secured using adhesive or mechanical attachment means. Mirror assembly 11 also includes a head portion 17 that is secured to stem 13. Stem 13 and head portion 17 may be a unitary member, created by injection molding or the like. Head portion 17 includes a receptacle 18 which is adapted to receive mirror housing 16 therein. Receptacle 18 includes a plurality of retention holes 19 which align with, and are adapted to receive snaps 20 which extend from the bottom surface of mirror housing 16. When mirror housing 16 is received in receptacle 18, snaps are received in retention holes 19, thereby securing mirror housing 16 thereto.

A scratched or defective mirror 14 may be replaced by using a fingernail or blunt object to pry mirror housing 16 from head portion 17. The snaps 20 are thereby disengaged from retention holes 19 and a new mirror 14 and mirror housing 16 may thereafter be secured to head portion 17.

Figure 2:
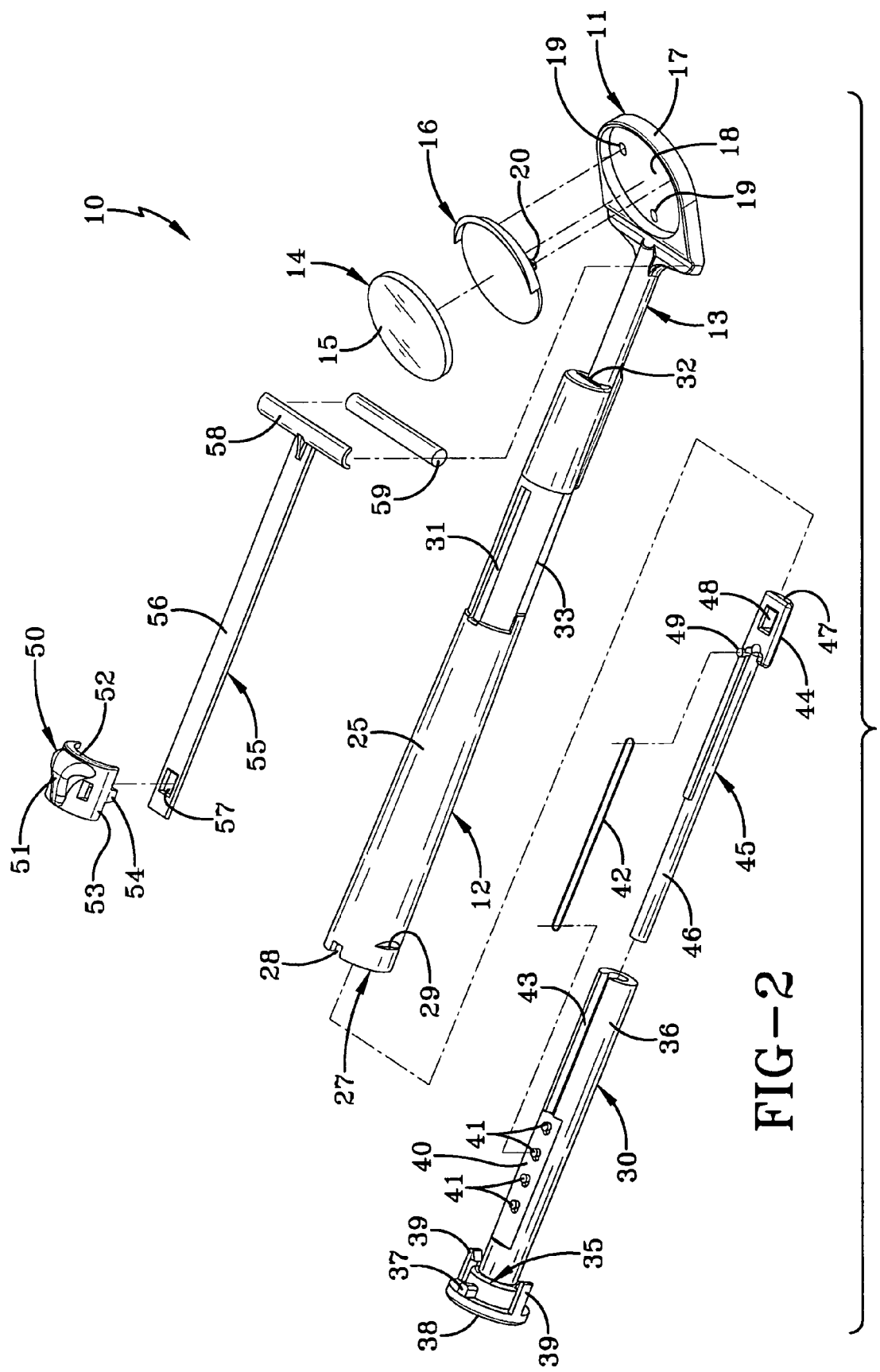
FIG. 2 is an exploded view of the dental mirror of FIG. 1.
Figure 4:
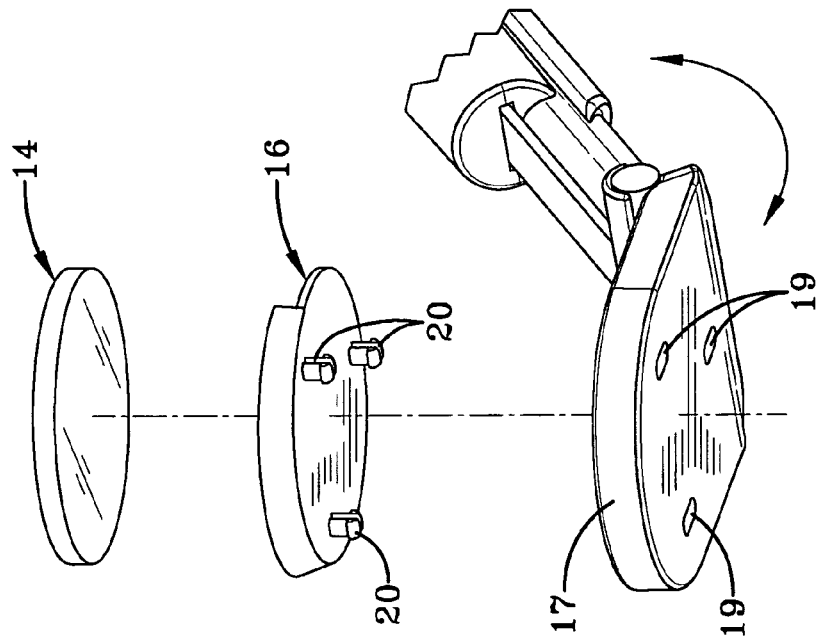
FIG. 4 is an exploded view showing the mirror head assembly.
Figure 3:
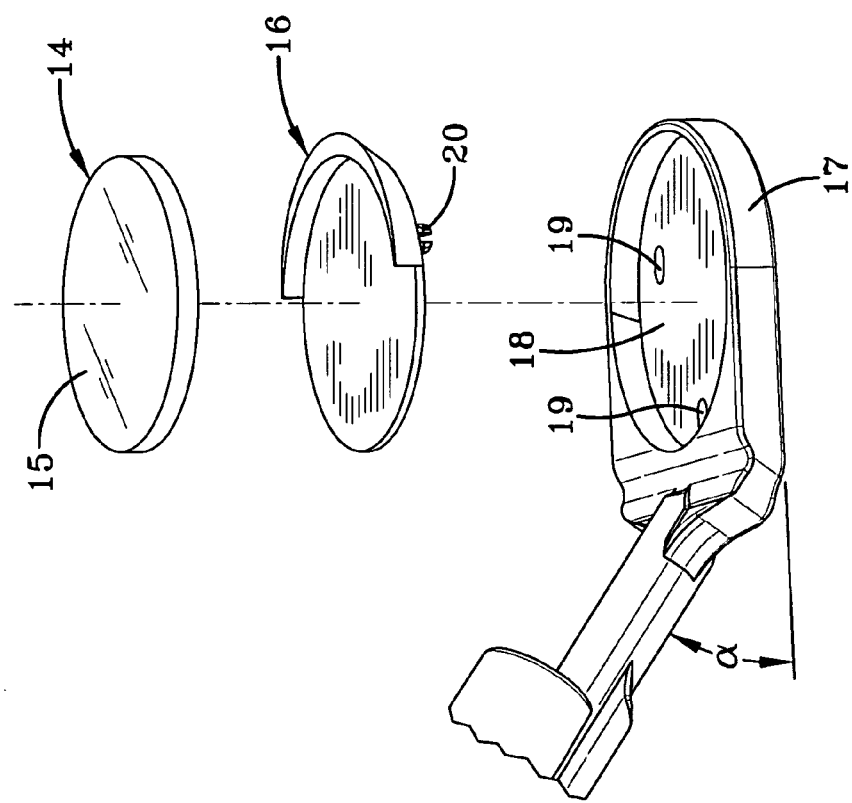
FIG. 3 is an exploded view showing the mirror head assembly.

Referring now to FIGS. 1 and 2, handle assembly 12 includes an elongate body portion 25 which may be generally cylindrical. Handle 12 is hollow, defining an interior cavity 26. A rear opening 27 is disposed at the rear end of body portion 25 and communicates with interior cavity 26. A notch 28 may be provided proximate to rear opening 27. Further, a pair of diametrically opposed detents 29 may be provided proximate to rear opening 27. As will become apparent, notch 28 and detents 29 are adapted to orient and secure an insert, generally indicated by the numeral 30, within interior cavity 26.

Handle 12 further includes an elongate slot 31 along the top of body portion 25. Elongate slot 31 communicates with interior cavity 26, and extends along the major axis of handle 12. Still further, handle 12 includes an aperture 32 on the end proximate to mirror assembly 11. Aperture 32 may be non-circular. For example, as shown in FIGS. 1 and 2, aperture 32 may be generally rectangular and aligned with the flat surface of stem 13. Handle 12 may further include a pair of opposed undercuts 33 running along the major axis.

Insert 30 includes an end cap 35 and an elongate body 36. End cap 35 includes a projection 37 which is sized to fit within notch 28 when elongate body 36 is positioned within interior cavity 26. In this manner, insert 30 is indexed to the correct operating position. As is evident from FIG. 1, end cap 35 includes a base portion 38 which is larger than rear opening 27 and thus rests against the back of body portion 25. A pair of clips 39 extend from the periphery of base portion 38 and are each received in a detent 29. In this manner, once the insert 30 is positioned within handle 12, clips 39 hold it in place. If disassembly is necessary, clips 39 are simply pried outwardly, and the insert 30 may be removed.

The elongate body 36 of insert 30 is sized to fit snugly within interior cavity 26 of handle 12. Elongate body 36 is provided with a flattened top portion 40 from which a plurality of lugs 41 extend. Lugs 41 are longitudinally spaced and are adapted to receive one end of an elastic member, preferably in the form of a rubber-band 42 thereon. A channel 43 is also provided which extends from flattened portion 40 to the front end of elongate body 36. As is evident from FIG. 5, channel 43 provides a recess which receives an elastic member such as rubber-band 42 therein. While a rubber-band is shown in the present embodiment, other elastic members may be used such as, for example, a spring. Channel 43 further receives and guides a portion of a slider, generally indicated by the numeral 45, as will be hereinafter described.

Figure 5:
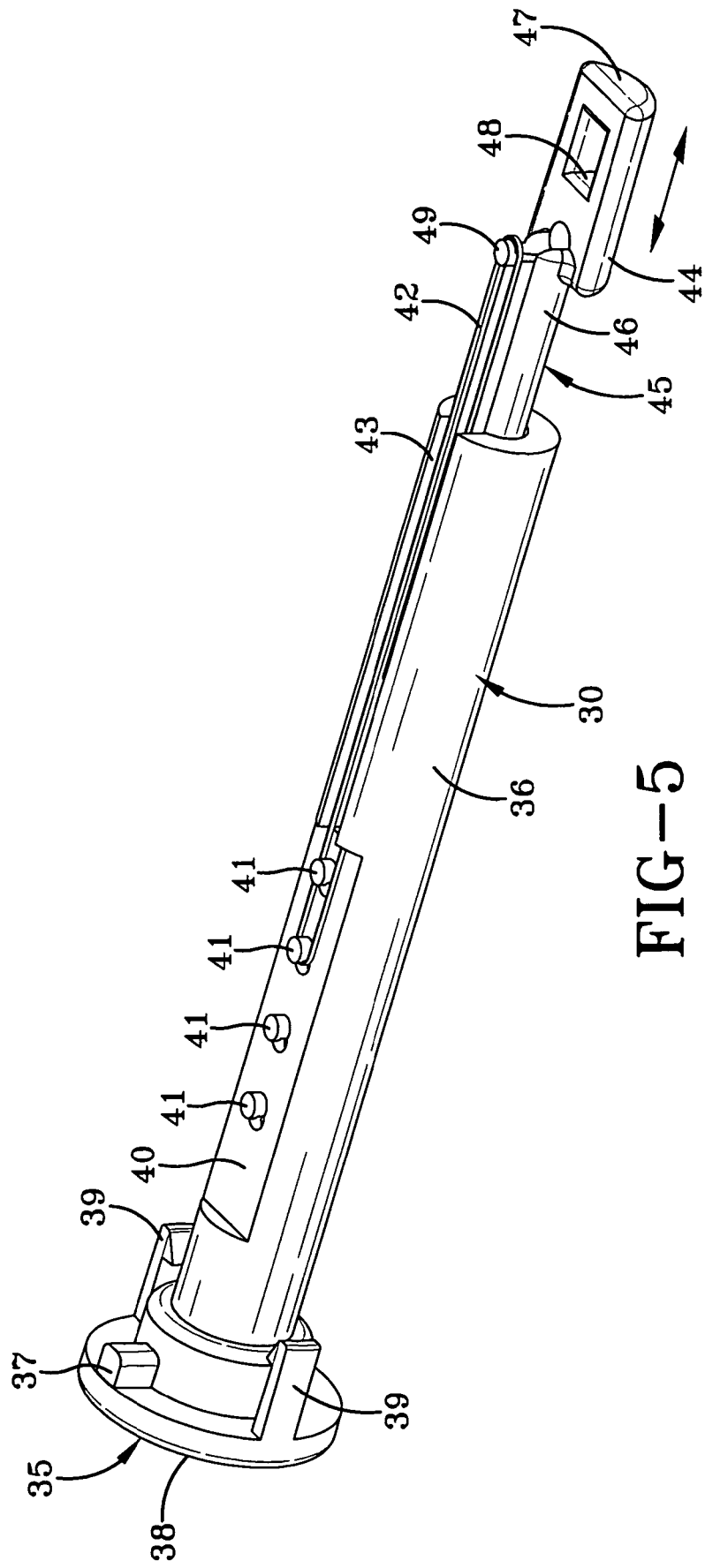
FIG. 5 is an exploded view showing the slider in its active position.

Slider 45 is provided with an arm 46 which may be generally rectangular in cross-section. As shown in FIG. 5, arm 46 is slidably received within channel 43. Arm 46 is longer than channel 43 and consequently, extends forwardly from insert 30. A sled 47 extends from the forward end of arm 46 and includes a bottom portion 44 which is shaped to match the profile of interior cavity 26. Sled 47 includes a hook 49 which is adapted to receive the other end of rubber-band 42 thereon. In this manner, slider 45 is biased toward insert 30. In other words, slider 45 is pulled rearwardly by rubber-band 42. Sled 47 further includes an upwardly facing aperture 48 which, as will become apparent, receives a portion of a thumb tab 50 therein.

Thumb tab 50 includes a finger contact surface 51 which is adapted to allow a user to apply a force to thumb tab 50. Thus, finger contact surface 51 may be disposed at an angle relative to elongate body portion 25. Thumb tab 50 is slidable on handle 12 and thus includes a curved body portion 52 which generally matches the profile of handle 12. A pair of clips 53 extend downwardly from the sides of body portion 52 and engage undercuts 33. In this manner, thumb tab 50 is held to handle 12 but is capable of sliding movement along the major axis thereof.

Figure 6:
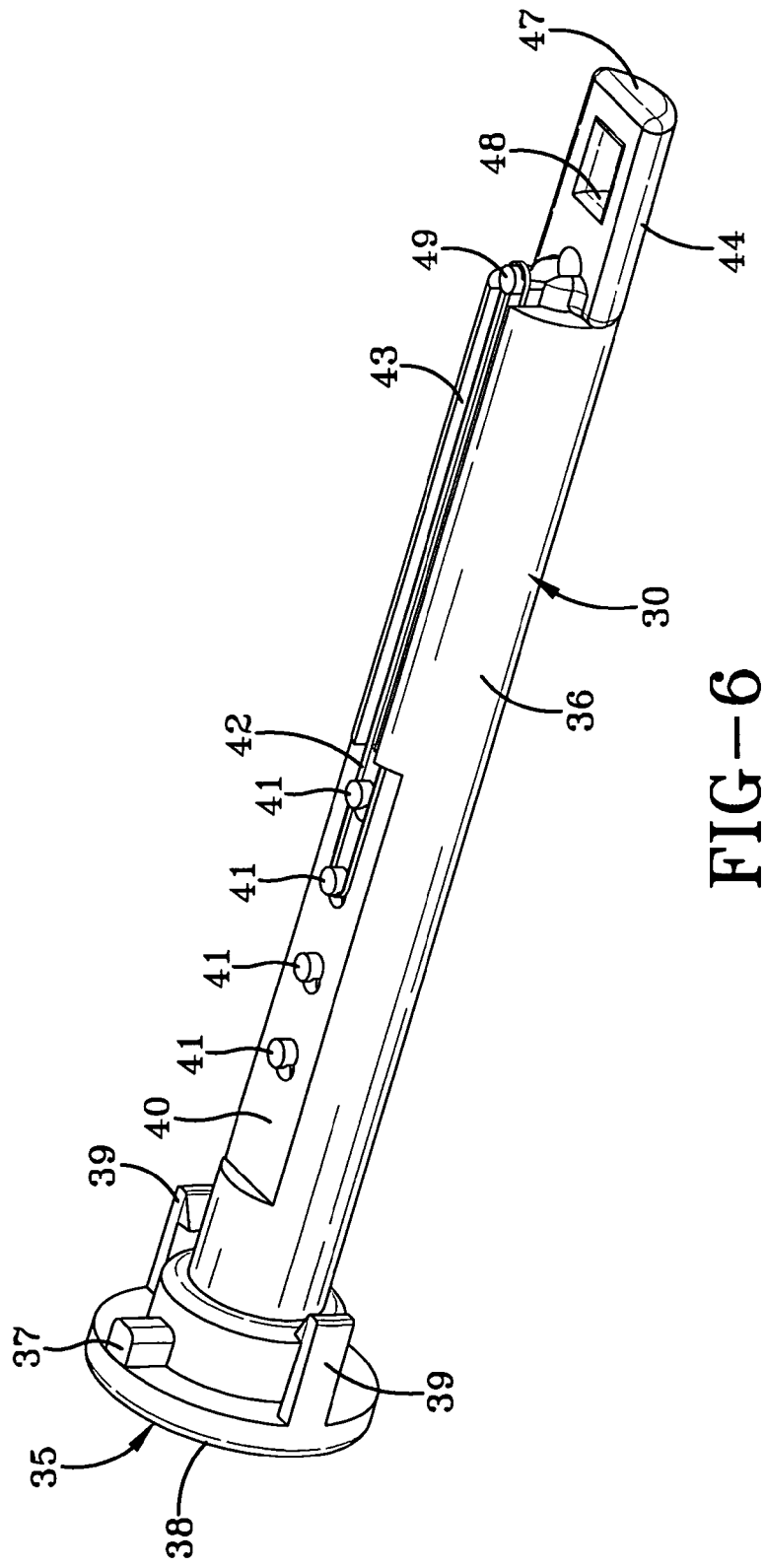
FIG. 6 is an exploded view showing the slider of the present invention in a retracted position.
Figure 7:
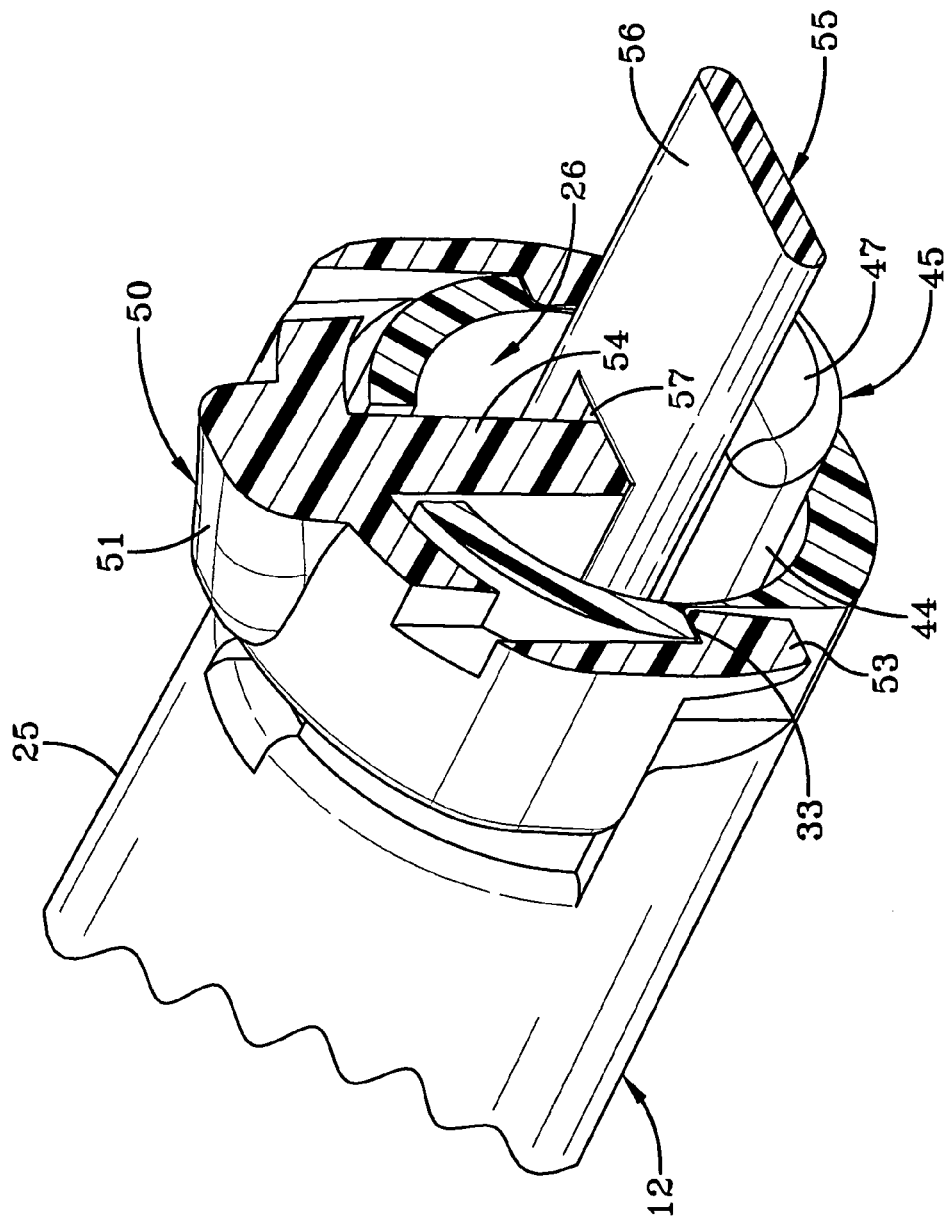
FIG. 7 is a partial sectional view of the dental mirror.

Thumb tab 50 includes an interior post 54 which extends inwardly through elongate slot 31. Slot 31 is sized to allow bind-free movement while effectively aligning and guiding thumb tab 50. Post 54 is received within aperture 48 of slider 45 and is in this manner, is operatively interconnected thereto. Thus, as thumb tab 50 is pushed forward by a user, slider 45 correspondingly is forced forwardly. As is evident from FIGS. 5-7, this forward movement is resisted by the bias force of rubber-band 42.

A push-arm 55 is also operatively interconnected to with thumb tab 50, so that forward movement of thumb tab 50 causes forward movement of push-arm 55. Push-arm 55 includes an extension 56 which is elongate, having a portion residing within cavity 26 and a portion which is outside cavity 26. Extension 56 is composed of an elastically resilient material which allows it to flex and return to its original form and includes an upwardly facing aperture 57 proximate the rear end. Aperture 57 is aligned with aperture 48 so that, when assembled, post 54 is received within both. In this manner, slider 45, thumb tab 50 and push-arm 55 are coupled together. As shown in FIG. 1, extension 56 extends from interior cavity 26 through aperture 32 at the front of handle 12. Aperture 32 is closely toleranced so that extension 56 may easily slide therethrough, yet it still provides support and guidance. In other words, the cross-sectional shape of extension 56 corresponds to, but is slightly smaller than, the shape of aperture 32. In the present embodiment, aperture 32 is generally rectangular. It should thus be apparent that when a non-circular aperture 32 is provided, rotation of extension 56 is prevented. This feature enhances stability of push-arm 55 and enables the elimination of additional support structure on mirror assembly 11.

Push-arm 55 includes a wiper support 58 at the forward end of extension 56. Wiper support 58 may have a generally "C" shaped cross-section and receives a wiper sponge 59 therein. Wiper sponge 59 is preferably secured within wiper support 58 via an adhesive. Wiper sponge 59 is made of an absorbent material that is adapted to soak up anti-fog solutions.

Dental mirror 10 may be used in the following manner. Prior to insertion into an oral cavity, mirror assembly 11 and wiper support 58 are dipped briefly into an anti-fog solution. After removal from the anti-fog solution, a thin film of anti-fog solution remains on reflective surface 15. Also, the wiper sponge is saturated with the anti-fog solution. The mirror may then be used as known in the art. Once reflective surface 15 becomes clouded, either by fogging or by fluids from the oral cavity, the user applies a forwardly directed force to thumb tab 50. The thumb tab is thereafter caused to slide forward and, in turn, push arm 55 slides forwardly. The forward movement of push-arm 55 causes wiper sponge 59 to engage reflective surface 15. The user continues to push thumb tab 50 forward until wiper sponge 59 is drawn forwardly along the entire reflective surface 15. Because extension 56 is a thin, resilient material, it will elastically deflect as it contacts the angled surface of mirror 14. In this manner a downward force is applied to reflective surface 15, which aids in cleaning and application of the anti-fog solution.

Once push-arm is fully extended, the user may then release thumb tab 50 and the rubber-band automatically retracts slider 45, thumb tab 50 and push-arm 55. This in turn pulls wiper sponge rearwardly along reflective surface 15 and back to the initial unactuated position. This forward and rearward motion of wiper sponge 59 cleans reflective surface 15 and leaves a thin film of anti-fog solution thereon. Dental mirror 10 is then again ready for use.

It should, therefore, be appreciated that a dental mirror assembly constructed as described herein, accomplishes the objects of the invention and substantially improves the art.

What is claimed is:

1. A dental mirror instrument comprising a handle having an elongate body portion defining an interior cavity, said elongate body portion having first and second openings at the opposed ends of said elongate body portion, said handle further including an elongate slot which communicates with said interior cavity, an insert received in said first opening and including at least one lug, a slider slidably received in said interior cavity and including a hook, wherein said insert includes a channel positioned forward of said lugs, said slider including an arm slidably received in said channel, a thumb tab slidably coupled to said elongate body portion and including a post which extends through said elongate slot, a push-arm extending through said second opening and carrying a wiper thereon, and a mirror assembly positioned proximate said second opening and adapted to reflect light, wherein forward movement of said thumb tab correspondingly causes forward movement of said push-arm and said slider.

2. The dental mirror instrument according to claim 1, further including an elastic member, said elastic member biasing said push-arm in a direction opposed from said mirror assembly.

3. The dental mirror instrument according to claim 1, further including an anti-fog solution wherein said wiper includes a wiper sponge, which is adapted to absorb an anti-fog solution.

4. The dental mirror instrument according to claim 1, wherein said mirror assembly includes a head portion coupled to said handle and at least one retention hole, a mirror housing which receives a mirror, said mirror housing having at least one snap, wherein said snap is received within said retention hole to couple said mirror housing to said head portion.

5. The dental mirror instrument according to claim 4, further comprising a stem, said stem coupling said head portion to said handle.

6. The dental mirror instrument according to claim 1, wherein said slider includes a first aperture and said push-arm includes a second aperture, said post being received within said first and said second aperture.

7. The dental mirror instrument according to claim 1, further including a rubber-band, said rubber-band being received on said lug and said hook to bias said slider away from said mirror assembly.

8. The dental mirror instrument according to claim 1, wherein said elongate body includes opposed undercuts along the major axis of said elongate body portion, and said thumb tab includes a pair of clips which engage said undercuts, coupling said thumb tab to said handle.

9. The dental mirror instrument according to claim 1, wherein said channel receives said rubber-band therein.

10. The dental mirror instrument according to claim 1, wherein said slider further includes a sled having a bottom portion being shaped to match the profile of said interior cavity.

11. The dental mirror instrument according to claim 1, wherein said thumb tab includes a finger contact surface disposed at an angle relative to said elongate body portion.

* * * * *